United States Patent [19]

Browning et al.

[11] Patent Number: 5,554,108
[45] Date of Patent: Sep. 10, 1996

[54] SANITARY TAMPON

[75] Inventors: John H. D. Browning, Alresford; Robert I. Wynne, Hayling Island, both of England; Harry Hayes, Hampden, Mass.

[73] Assignee: Tambrands Inc., White Plains, N.Y.

[21] Appl. No.: 240,669

[22] PCT Filed: Oct. 29, 1992

[86] PCT No.: PCT/GB92/01980

§ 371 Date: Jun. 29, 1994

§ 102(e) Date: Jun. 29, 1994

[87] PCT Pub. No.: WO93/08779

PCT Pub. Date: May 13, 1993

[30] Foreign Application Priority Data

Nov. 6, 1991 [GB] United Kingdom ............... 9123524

[51] Int. Cl.⁶ ........................................... A61F 13/20
[52] U.S. Cl. ................................. 604/15; 604/904
[58] Field of Search ...................... 604/1–3, 11–18, 604/904

[56] References Cited

U.S. PATENT DOCUMENTS 2,854,978  10/1958  Millman et al. ..................... 604/904
3,791,385  2/1974  Davis et al. ........................ 604/12
4,286,595  9/1981  Ring .................................... 604/14

FOREIGN PATENT DOCUMENTS 0252381  1/1988  European Pat. Off. .
0291343  11/1988  European Pat. Off. .

*Primary Examiner*—Randall L. Green
*Assistant Examiner*—Dennis Ruhl
*Attorney, Agent, or Firm*—Fish & Richardson P.C.

[57] ABSTRACT

The present invention relate to a sanitary tampon comprising a compact applicator and a tampon (3) of compressed absorbent material stored within the applicator, the applicator having an inner tube (1) and an outer tube (2) slidably disposed over the inner tube (1). The outer tube (2) has a distal discharge end (4) for insertion into the body of the user. The tampon (3) is solid and substantially cylindrical in shape and is constructed such that at least a part of the body (11) of the tampon (3) adjacent the proximal end (13) sits at an angle to the longitudinal axis of the applicator so that when the inner tube (1) is withdrawn past the proximal end (13) of the tampon (3) to prime the applicator for use, the proximal end (13) of the tampon will urge itself against the inner surface of the outer tube (2) and when the inner tube (1) is pushed back into the outer tube (2) to expel the tampon, the tampon is hindered from re-entering the distal end (6) of the inner tube (1).

14 Claims, 2 Drawing Sheets

SANITARY TAMPON

CROSS-REFERENCES TO RELATED APPLICATIONS

This application is a National Phase Filing of PCT/GB92/01980, filed Oct. 29, 1992, based on priority document GB 9123524.2, filed Nov. 6, 1991.

The present invention relates to sanitary tampons which comprise an applicator for placing a tampon in position within the body of a user of the tampon.

BACKGROUND OF THE INVENTION

It is known to provide applicators in which an outer tube for storing a tampon therein has a distal discharge end for insertion into the body and the tampon is ejected by slidably moving an inner tube within the outer tube.

In order to provide less bulky applicators, a number of arrangements have been proposed in which the inner tube is initially received telescopically within the outer tube and must be partially withdrawn before the dispensing operation. Such an arrangement is known as a "compact applicator". However, it has been found in compact applicators that once the inner tube has been partially withdrawn and the applicator is primed for use, the inner tube will often pass back between the tampon and the inner surface of the outer tube when the user pushes the inner tube inwards to discharge the tampon into the body. When this occurs, the inner tube will simply relocate itself between the tampon and the outer tube without discharging the tampon—this effect is often referred to as "re-tubing".

In International patent application No. PCT/GB 90/01651 (WO 91/06272), the applicants proposed a tampon applicator which aimed to overcome the problem of "re-tubing". However, this applicator made use of a complex slot and protruding tab arrangement between the inner and outer tubes. In order to manufacture the applicator, complicated tooling is required and the fact that the inner tube has to be placed in a specific orientation within the outer tube makes automated assembly difficult. A further characteristic of this applicator is that if the user tries to discharge the tampon from the outer tube without first partially withdrawing the inner tube to prime the applicator for use, the inner tube can be freed from the outer tube by disengaging the tab which is intended to lock the inner and outer tubes together. If the inner tube is then partially withdrawn from the outer tube, there is no means to prevent complete withdrawal. These problems can be inconvenient. Therefore, successful operation relies heavily on the use of reading and understanding the instructions provided.

U.S. Pat. No. 4,726,805 also describes tampon applicators which are intended to overcome the problem of "re-tubing". The applicators are made from a deformable/flexible material such as a thermoforming plastic to ensure that the product functions correctly. Accordingly, the plastic applicators do not provide environmentally friendly and convenience of disposal advantages such as biodegradability and flushability. Further disadvantages associated with the plastic applicator are that the costs of moulding equipment are very high resulting in a higher unit cost for the applicator.

The present invention, therefore, seeks to overcome the disadvantages of the prior art applicators by providing a simpler, user friendly product which is still able to overcome the typical problems encountered by users.

SUMMARY OF THE INVENTION

According to the present invention there is provided a sanitary tampon comprising a compact applicator and a tampon of compressed absorbent material stored within the applicator, the applicator having an inner tube and an outer tube slidably disposed over the inner tube, the outer tube having a distal discharge end for insertion into the body of the user wherein the tampon is solid and substantially cylindrical in shape, characterised in that the tampon is constructed such that at least a part of the body of the tampon adjacent the proximal end always sits at an angle to the longitudinal axis of the applicator so that when the inner tube is withdrawn past the proximal end of the tampon to prime the applicator for use, the proximal end of the tampon will urge itself against the inner surface of the outer tube and when the inner tube is pushed back into the outer tube to expel the tampon, the tampon is hindered from re-entering the distal end of the inner tube.

The advantage with such a tampon applicator is that the tampon itself is able to prevent "re-tubing" so that the construction of the inner and outer tubes can be kept as simple as possible. This avoids the need for special machinery to cut, orientate and assemble tubes with elaborate slots or tabs. Furthermore, because the finished product is streamlined in appearance, it is particularly atractive to the user.

Preferably, the outer surface of the tampon body is provided with a projection which causes the body of the tampon to sit at an angle to the longitudinal axis of the applicator.

Preferably, the tampon body is curved below the distal end.

Preferably, the tampon body is slanted with respect to its distal end.

Preferably, the longitudinal axis of the tampon body is not coincident with that of the tampon head.

Preferably, the outer surface of the tampon body is provided with an indentation.

Preferably, the distal end of the tampon has an enlarged head, part of which sits coaxially with respect to the longitudinal axis of the applicator.

Preferably, the widest part of the enlarged head sits firmly within the distal end of the outer tube to anchor the head such that the axis of the tampon body is not coaxial with that of the applicator.

Preferably, the outer and inner tubes are provided with means to limit withdrawal of the inner tube from the outer tube.

Preferably, the proximal end of the outer tube is cupped inwardly and the outer surface of the distal end of the inner tube is provided with a rim which abuts the proximal end of the outer tube to limit withdrawal.

Preferably, the distal end of the inner tube is cupped inwardly.

Preferably, the proximal end of the tampon is enlarged.

Preferably, the length of the applicator before preparation for use is substantially no greater than the length of the tampon.

Preferably, the tampon comprises a compressed fibrous cellulosic absorbent material.

BRIEF DESCRIPTION OF THE DRAWINGS

Preferred embodiments of the present invention will now be described in detail, by way of example only, with reference to the accompanying drawings, of which.

DESCRIPTION OF THE PREFERRED EMBODIMENTS

Figure 1:
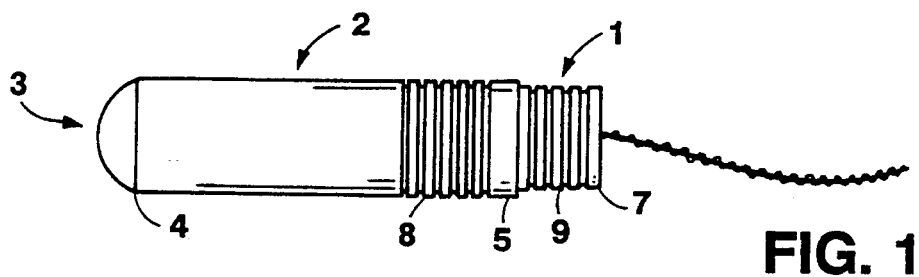
FIG. 1 depicts a sanitary tampon according to a first preferred embodiment of the present invention when the tampon is in its stored position.
Figure 2:
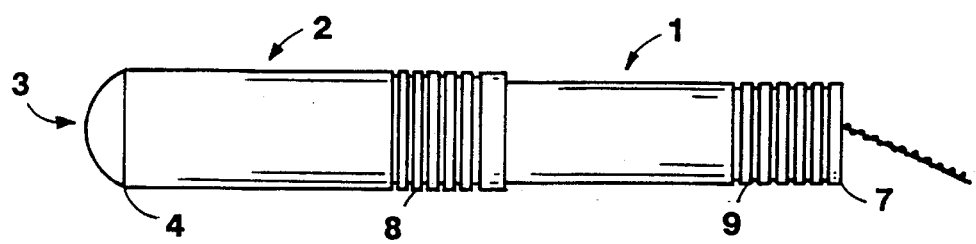
FIG. 2 depicts the sanitary tampon in FIG. 1 when the inner tube of the application has been withdrawn to prime the applicator for use.

FIG. 1 depicts a sanitary tampon which comprises an applicator having an inner tube 1 and an outer tube 2 and a tampon 3 of compressed absorbent material stored within the applicator. The inner and outer tubes 1, 2 are constructed by spirally winding layers of paper and bonding the layers with a suitable adhesive. The outer tube 2 has an open distal end 4 which is inserted into the body of the user and an open proximal end 5. The inner tube 1 also has an open distal end 6 (see FIG. 4) and an open proximal end 7. A series of circumferential grooves 8, 9 are provided on the proximal end of the outer and inner tubes respectively to facilitate gripping of the applicator by a user.

The inner and outer tubes can be manufactured in paper, cardboard or plastic depending on end requirements.

Figure 4:
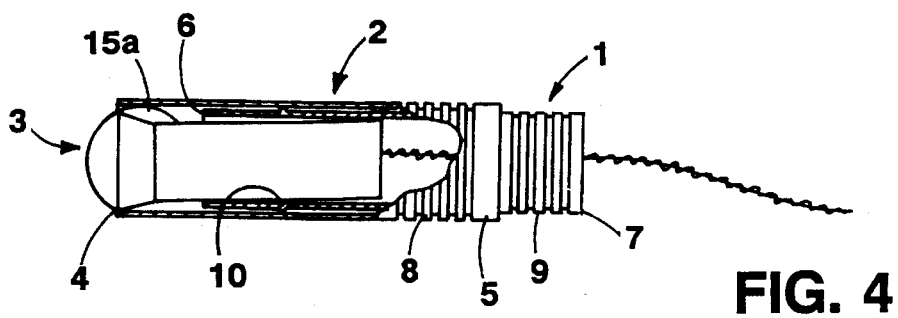
FIG. 4 is a view of the interior of the sanitary tampon in FIG. 1.

If one refers to FIG. 4 which depicts the interior of the applicator in FIG. 1, it is clear that the inner tube 1 is cupped inwardly at its distal end 6 and is provided with a circumferential rim 10 on its outer surface. In addition, the proximal end 5 of outer tube 2 is cupped inwardly. The cupping of the inner and outer tubes and rim 10 will be explained in detail with respect to the operation of the tampon applicator.

Figure 3:
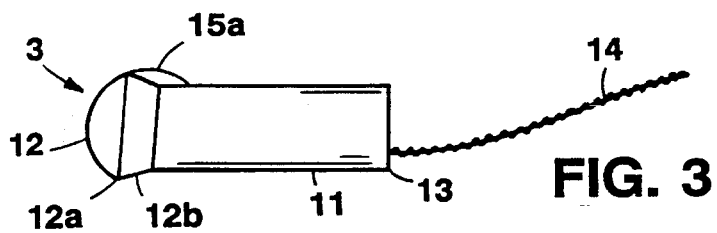
FIG. 3 depicts separately the tampon which is stored in the applicator in FIGS. 1 and 2.

FIG. 3 depicts a preferred embodiment of a tampon 3 which can be used in the applicator depicted in FIG. 1. The tampon 3 is constructed such that it is asymmetrical having a nib 15a on one side of the body 11 of the tampon just below the enlarged head 12. The tampon 3 is also provided with a withdrawal cord 14. The tampon 3 has an enlarged head 12 comprising a rounded tip 12a and a tapered portion 12b the widest part of the tampon being the region where the tip 12a and tapered portion 12b meet. The widest part of the head 12 is a firm fit in the applicator and will sit substantially coaxially with respect to the longitudinal axis of the applicator. The enlarged head 12 will act as a limiting means to prevent the tampon from being pulled into the outer tube 2 when the inner tube 1 is withdrawn to prime the applicator for use.

It can be seen that when the tampon 3 is stored within the inner tube 1 the nib 15a will cause the proximal end 13 of the tampon 3 to be urged against the inside of inner tube 1 and thus the tampon body will sit at an angle to the longitudinal axis of the applicator. In order that the asymmetry of the tampon body functions as required, the angle at which the tampon body sits with respect to the longitudinal axis of the applicator should be between 1° and 3° preferably 2.5°. The widest part of the enlarged head 12 of the tampon 3 will act to anchor the tampon at its distal end thereby further urging the proximal end 13 into contact with the inner tube 1.

The tampon 3 can be made in any conventional manner, i.e by compressing a flat pad or a spirally wound construction. Preferably, the tampon 3 is made from a compressed fibrous cellulosic absorbent material.

Figure 5:
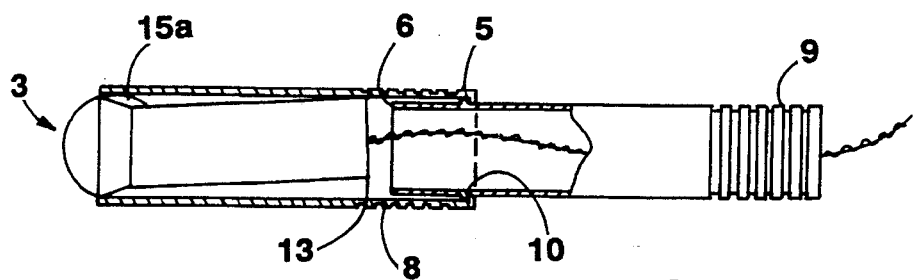
FIG. 5 is a view of the interior of the sanitary tampon in FIG. 2.

FIG. 5 depicts the tampon and applicator when the inner tube 1 has been partially withdrawn from the outer tube 2 to prime the applicator for use. The cupping on the proximal end 5 of the outer tube 2 and the rim 10 on the inner tube 1 will ensure that the inner tube 1 is not completely withdrawn from the outer tube 2. When the distal end 6 of the inner tube 1 is pulled past the proximal end 13 of tampon 3, the asymmetric construction of tampon 3 will urge the proximal end 13 against the inner surface of outer tube 2. In this way, when the inner tube 1 is pushed back into the outer tube 2 to expel the tampon 3, the proximal end 13 of the tampon will not re-enter the distal end 6 of the inner tube 1. The cupping of the distal end 6 of the inner tube 1 also ensures that "re-tubing" does not occur. A further embodiment of the present invention could comprise a tampon having an enlarged proximal end 13 to further ensure that "re-tubing" is unlikely.

FIGS. 6, 7, 8 and 9 depict further embodiments of tampons which would sit at an angle within the applicator.

Figure 6:
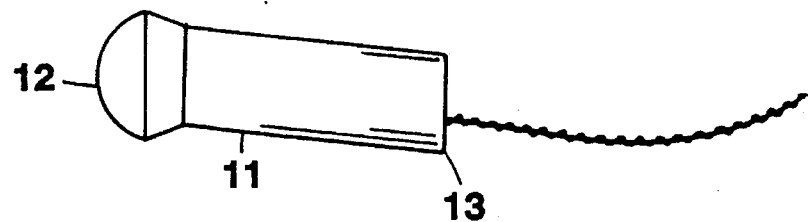
FIG. 6 depicts a further embodiment of a tampon which could be used with the applicator in FIG. 1.
Figure 7:
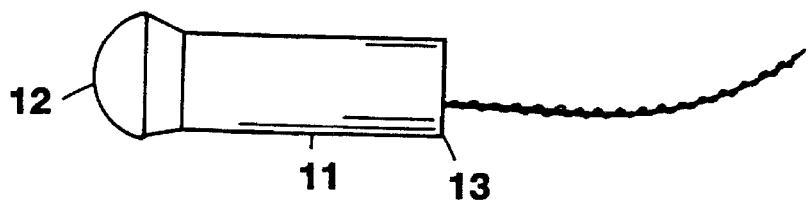
FIG. 7 depicts another embodiment of a tampon which could be used with the applicator shown in FIG. 1.
Figure 8:
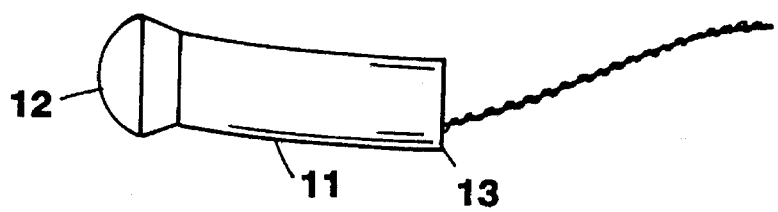
FIG. 8 depicts yet another embodiment of a tampon which could be sued with the applicator shown in FIG. 1.
Figure 9:
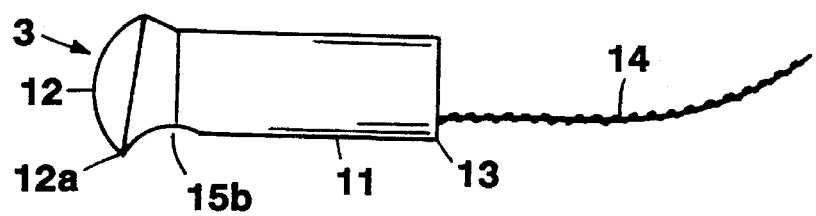
FIG. 9 depicts still another embodiment of a tampon which could be used with the applicator shown in FIG. 1.

In FIG. 6 the body 11 is formed at an angle to the head 12 of the tampon. In FIG. 7 the head 12 is offset from the longitudinal axis of the body 11. In FIG. 8 the body 11 is curved with respect to the head 12. FIG. 9 depicts a tampon having an indentation 15b. This indentation is formed during compression of the tampon and the induced asymmetry will cause the resulting tampon body 11 to sit at an angle to the longitudinal axis of the applicator when the head 12 is held in the outer tube. Each construction will sit at an angle to the longitudinal axis of the applicator adjacent the proximal end 13 thus urging the tampon into contact with the inner surface of the inner tube 1 or outer tube 2 when the inner tube is withdrawn. By sitting at an angle the risk of the proximal end 13 "re-tubing" in the distal end 6 of the inner tube 1 is minimal, particularly if the distal end 6 of inner tube 1 is cupped inwardly and the proximal end 13 of the tampon is slightly enlarged.

Thus, it can be seen that the problem of "re-tubing" is overcome simply by constructing the tampon in a particular manner without the need for a complicated construction of inner and outer tubes. Clearly, the relative dimensions of the tampon, the inner tube and the outer tube will have to be chosen carefully to ensure smooth operation of the applicator. It is envisaged that the length of the applicator before preparation for use could be substantially no greater than that of the tampon itself thereby further increasing its discreteness, ease of carrying and aesthetic appeal.

We claim:
1. A sanitary tampon assembly comprising
a compact applicator comprising an inner tube and an outer tube slidably disposed over the inner tube so that a major portion of the inner tube is telescopically retained inside the outer tube, the outer tube having a distal discharge end shaped for insertion into the body of a user, the inner tube having distal and proximal ends; and a tampon, having a distal expulsion end and a proximal withdrawal end and comprising a solid body formed of compressed absorbent material, a major portion of said tampon being disposed inside the inner tube, said tampon having a tampon longitudinal axis extending from the distal expulsion end to the proximal withdrawal end, said tampon being shaped and dimensioned so that when the tampon is positioned in the inner tube, said tampon longitudinal axis extends at an angle with respect to a longitudinal axis of the applicator, taken lengthwise through an approximate center of the inner tube, and, when the inner tube is withdrawn past the proximal end of the tampon to remove the tampon from the inner tube and thereby prime the applicator for use, the proximal end of the tampon will asymmetrically urge itself against one side of an inner surface of the outer tube so that, when the inner tube is pushed back into the outer tube to expel the tampon, the proximal end of the tampon will be hindered from re-entering the distal end of the inner tube.

2. A sanitary tampon assembly as claimed in claim 1 wherein an outer surface of said tampon is provided with a projection which causes said portion of said tampon to extend at said angle with respect to the longitudinal axis of the applicator.

3. A sanitary tampon assembly as claimed in claim 1 wherein a distal region of said tampon includes an indentation shaped and positioned to cause said portion of said tampon to extend at said angle with respect to the longitudinal axis of the applicator.

4. A sanitary tampon assembly as claimed in claim 1 wherein a longitudinal axis taken through the approximate center of said portion of said tampon extends at an angle with respect to a longitudinal axis taken through a second portion of said tampon adjacent said distal end of said tampon.

5. A sanitary tampon assembly as claimed in claim 1 wherein an outer surface of said tampon is provided with an indentation.

6. A sanitary tampon assembly as claimed in any preceding claim wherein said distal end of the tampon has an enlarged head, part of which is positioned coaxially with respect to said longitudinal axis of the applicator.

7. A sanitary tampon assembly as claimed in claim 6 wherein a portion of the enlarged head sits firmly within said distal end of the outer tube to anchor the head in a position in which a longitudinal axis taken through an approximate center of said portion of said tampon is not co-axial with said longitudinal axis of the applicator.

8. A sanitary tampon assembly in claim 1 wherein the outer and inner tubes are provided with means to limit withdrawal of the inner tube from the outer tube.

9. A sanitary tampon assembly as claimed in claim 8 wherein proximal end of the outer tube is cupped inwardly and an outer surface of the distal end of the inner tube is provided with a rim which abuts a proximal end of the outer tube to limit withdrawal.

10. A sanitary tampon assembly as claimed in claim 1 wherein said distal end of the inner tube is cupped inwardly.

11. A sanitary tampon assembly as claimed in claim 1, wherein the proximal end of the tampon is enlarged.

12. A sanitary tampon assembly as claimed in claim 1 wherein the length of the applicator before preparation for use is substantially no greater than the length of the tampon.

13. A sanitary tampon assembly as claimed in claim 1, wherein the tampon comprises a compressed fibrous cellulosic absorbent material.

14. A sanitary tampon assembly as claimed in claim 1 wherein said tampon is asymmetrically shaped about said tampon longitudinal axis.

* * * * *